United States Patent [19]

Andersen et al.

[11] Patent Number: 5,302,358
[45] Date of Patent: Apr. 12, 1994

[54] STERILIZING APPARATUS

[75] Inventors: Harold W. Andersen, Oyster Bay, N.Y.; Charles H. Harrison, Haw River, N.C.

[73] Assignee: H. W. Andersen Products, Inc., Oyster Bay, N.Y.

[21] Appl. No.: 6,030

[22] Filed: Jan. 15, 1993

[51] Int. Cl.⁵ .......................... A61L 2/20; B05B 11/04
[52] U.S. Cl. ..................................... 422/305; 206/528; 206/532; 222/80; 222/135; 239/373; 422/292; 422/294; 422/297; 422/300
[58] Field of Search ............... 422/292, 294, 297, 300, 422/305; 206/532, 528; 239/373; 222/80, 135

[56] References Cited

U.S. PATENT DOCUMENTS

| | | |
|---|---|---|
| 3,476,506 | 11/1969 | Andersen et al. |
| 3,505,775 | 6/1966 | Andersen et al. |
| 4,528,268 | 7/1985 | Andersen et al. ........... 435/31 |
| 4,779,763 | 10/1988 | Klawitter ..................... 222/80 |
| 4,937,046 | 6/1990 | Andersen et al. ........... 422/294 |

Primary Examiner—Jill A. Johnston
Attorney, Agent, or Firm—Jordan and Hamburg

[57] ABSTRACT

Apparatus for sterilizing objects with a gaseous ethylene oxide held in a sealed ampule of the type including a breakable section, includes a cartridge for holding the sealed ampule in a substantially immovable manner, the cartridge including a first chamber for containing the ampule, a second chamber for holding an absorbent cotton material to hold the liquid sterilant upon breaking open of the ampule, the first and second chambers being in communication with each other, a transverse bore extending into the first chamber and outlet openings in the second chamber; a push-button slidably movable in the transverse bore for breaking open the ampule upon depression of the push-button in the transverse bore, wherein, upon breaking open the ampule, the gaseous sterilant escapes from the ampule through the outlet openings into sterilizing contact with the objects; a releasable guard for preventing slidable movement of the push-button in the transverse bore to prevent breaking of the ampule; and a liner bag for holding the cartridge and the objects to be sterilized in a sealed manner.

18 Claims, 3 Drawing Sheets

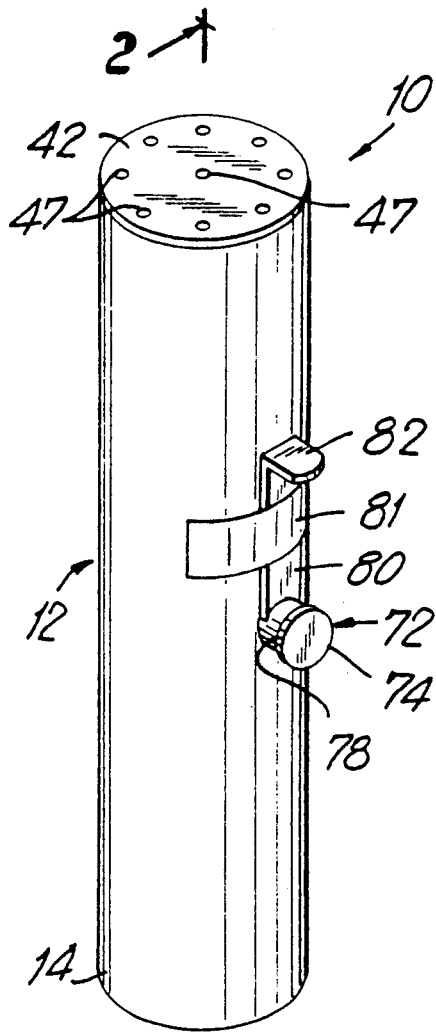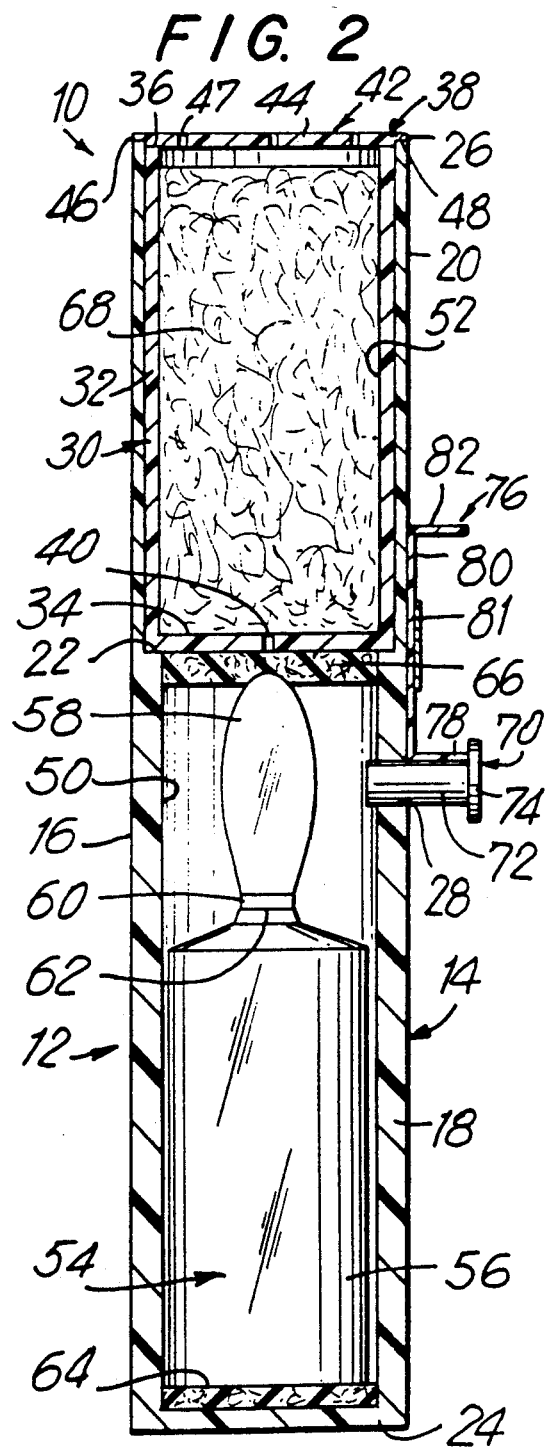

STERILIZING APPARATUS

BACKGROUND OF THE INVENTION

The present invention relates generally to an apparatus for sterilizing objects and, more particularly, is directed to a novel actuating mechanism for a sterilization apparatus.

It is well known to sterilize surgical, medical, dental and other instruments and the like by exposing them to a gaseous sterilant in a closed container. In order to provide an arrangement that can be readily used for the sterilization of instruments, it is further known to provide the gaseous sterilant in an ampule, as disclosed, for example, in U.S. Pat. No. 3,476,506, having a common assignee herewith, the entire disclosure of which is incorporated herein by reference.

As disclosed therein, the ampule is in the form of a sealed gas-tight container made from a breakable material, such as glass, which is impervious to the sterilant. In order to provide for easy braking of the ampule, the ampule is preferably provided with a spout connected to the main body thereof by a reduced diameter neck, with the reduced diameter neck being provided with a score line for easy braking. The sterilant is preferably ethylene oxide, although any other suitable sterilant can be used. The ethylene oxide is maintained largely in a liquid state when sealed in the ampule.

The ampule is inserted and hermetically sealed in an inner plastic gas release bag or pouch made from a semi-permeable material such as polyethylene. In order to sterilize the instruments, the neck of the ampule is manually broken along the score line, while the ampule is in the gas release bag. As a result, the ethylene oxide boils so that all of the liquid is converted into gaseous form and released into the gas release bag to fill the same.

Thereafter, the gas release bag is inserted and sealed in an outer plastic liner bag, along with the instruments to be sterilized. Because the gas release bag is made from a semi-permeable material, the vapor of the sterilant will diffuse through the semi-permeable walls of the gas release bag at a rate which provides a sufficient concentration of sterilant within the liner bag to sterilize the instruments. The rate of diffusion of the sterilant through the walls of the gas release bag may be controlled by selecting the proper dimensions, thickness and pore size (i.e. permeability) of the gas release bag.

The liner bag is also made of a semi-permeable material, but provides a rate of diffusion to the atmosphere which does not permit a toxic level of the gaseous sterilant to reach the atmosphere surrounding the liner bag.

See also U.S. Pat. Nos. 3,505,775; 4,937,046; and 5,082,636, all having a common assignee herewith, and the entire disclosures of which are incorporated herein by reference.

With this arrangement, however, breaking of the ampule while it is in the gas release bag can become cumbersome, and during some times, difficult. This is because it is necessary to hold both the main body of the ampule and the spout separately, in order to break the neck along the score line, while the ampule is in the gas release bag.

Further, with such an arrangement, the permeability of the gas release bag is selected so that the peak concentration of the ethylene oxide in the liner bag occurs between two and three hours after the ampule has been broken. Because of this long time period, the user is able to break the ampule in the gas release bag, and then place the gas release bag within the liner bag, without being exposed to the gas.

However, if the gas release bag or pouch is fabricated of a highly porous, paper-like plastic material, such as that commonly sold under the trademark "TYVEK", the peak concentration of the gas is reached within the first ten minutes of release, yielding a higher initial ethylene oxide concentration and more rapid aeration from the same dose, where the dose is equal to the concentration multiplied by time. In such case, to provide protection for the user, the ampule must be broken while it is sealed in the gas release bag and while the gas release bag is sealed in the liner bag. As a result, it is more difficult to manipulate the ampule to break the same while the ampule is located in the sealed liner bag filled with objects to be sterilized, than in the case where the ampule is only in the gas release bag.

Further, with such an arrangement, no ethylene oxide is released by the gas release bag for about 15 minutes after the ampule is broken, and the peak concentration of ethylene oxide is reached in approximately 3 hours. It will be appreciated that this system is designed to operate at room temperature, and that the entire process takes approximately 38 hours, which includes a sterilization cycle that takes approximately 12 hours, followed by a 2 hour purging of the liner bag of ethylene oxide before the operator can open it safely, and followed lastly by a 24 hour cycle to air gas absorbent materials before they can be used. This operation, however, is unduly lengthy from a practical standpoint.

U.S. Pat. No. 4,528,268, also having a common assignee herewith, discloses an apparatus for testing the sufficiency of sterilization. With this apparatus, an ampule is held within a sleeve which, in turn, is held within a test tube. The test tube has a wedge-shaped bottom and the spout of the ampule faces the wedge-shaped bottom. An axially oriented plunger is slidably provided at the opposite open end of the test tube in order to bias the ampule downwardly in the axial direction of the test tube, whereupon the spout engages the wedge-shaped bottom and the ampule breaks along the score line.

However, there is no disclosure of using this apparatus for actually sterilizing objects in the manner taught by the aforementioned U.S. Pat. Nos. 3,476,506 and 5,082,636.

SUMMARY OF THE INVENTION

Accordingly, it is an object of the present invention to provide an apparatus for sterilizing objects that overcomes the problems with the aforementioned prior art.

It is another object of the present invention to provide an apparatus for sterilizing objects that permits easy and ready breaking of the sterilant-holding ampule while in the liner bag.

It is still another object of the present invention to provide an apparatus for sterilizing objects that uses a push-button to break the sterilant-holding ampule within a cartridge, while the cartridge is positioned within the liner bag.

It is yet another object of the present invention to provide an apparatus for sterilizing objects in which the push-button, cartridge and ampule can be shipped as a unit.

It is a further object of the present invention to provide an apparatus for sterilizing objects in which the push-button does not substantially increase the size and cost of the apparatus.

It is a still further object of the present invention to provide an apparatus for sterilizing objects in which the push-button is locked during shipping, to prevent accidental breaking of the ampule.

It is a yet further object of the present invention to provide an apparatus for sterilizing objects that eliminates the need for using a gas release bag.

It is another object of the present invention to provide an apparatus for sterilizing objects that reduces the time for sterilization.

It is still another object of the present invention to provide an apparatus for sterilizing objects that is relatively inexpensive and easy to make and use.

In accordance with an aspect of the present invention, an apparatus for releasing a gaseous sterilant held in a sealed ampule of the type including a breakable section, in order to sterilize objects, includes a cartridge for holding the sealed ampule in a substantially immovable manner, the cartridge including a transverse bore and at least one outlet opening; and a push-button slidably movable in the transverse bore for breaking open the ampule upon depression of the push-button in the transverse bore; wherein, upon breaking open the ampule, the gaseous sterilant escapes from the ampule through the at least one outlet opening into sterilizing contact with the objects.

Preferably, the cartridge has an elongated tubular configuration. In addition, because the ampule further includes a liquid sterilant, the cartridge includes a first chamber for containing the ampule, and a second chamber for holding an absorbent material to hold the liquid sterilant upon breaking open of the ampule, with the first and second chambers being in communication with each other. Sponge disks are positioned on opposite sides of the ampule in the first chamber for cushioning the ampule in the first chamber.

Specifically, in order to define the chambers, the cartridge includes an outer tubular shell having a closed first end and an open second end; and an inner tubular shell having a closed third end and an open fourth end, the inner tubular shell being inserted partially within the outer tubular shell through the open second end of the outer tubular shell, such that the first chamber is defined by the outer tubular shell and the closed first and third ends of the outer and inner tubular shells, respectively, and the second chamber is defined by the inner tubular shell and the closed fourth end of the inner tubular shell. The outer tubular shell includes a shoulder for defining the extent that the inner tubular shell is inserted into the outer tubular shell, and the closed fourth end of the inner tubular shell includes at least one opening for providing communication between the first and second chambers. In addition, a closure cap is provided for closing the open second and fourth ends of the outer and inner tubular shells, respectively, the closure cap including the at least one outlet opening therein.

The transverse bore is formed through the outer tubular shell at a position beneath the shoulder. The push-button includes a stem slidably movable in the transverse bore for breaking open the ampule upon depression of the push-button in the transverse bore, and a head connected with the stem for limiting slidable movement of the stem in the transverse bore.

A trigger guard is provided for preventing breaking of the ampule by the stem, and includes a C-shaped snap-lock in releasable engagement with the stem for preventing slidable movement of the stem in the transverse bore a sufficient distance to break the ampule, and a disengagement arm connected with the snap-lock for disengaging the snap-lock from the stem to permit slidable movement of the stem in the transverse bore a sufficient distance to break the ampule.

The ampule is of a conventional type that includes a main body, a spout and a reduced diameter neck which connects the main body and the spout, with the reduced diameter neck having a weakened section defined by a score line, which constitutes the breakable section. The stem is positioned to engage the spout when the stem is depressed in the transverse bore, so as to break the ampule along the weakened section.

The cartridge is held within a liner bag that holds the objects to be sterilized in a sealed manner, whereupon the ampule can be broken open by depression of the push-button while the ampule is in the liner bag.

The above and other objects, features and advantages of the invention will become readily apparent from the following detailed description thereof which is to be read in connection with the accompanying drawings.

BRIEF DESCRIPTION OF THE DRAWINGS

FIG. 1 is a perspective view of an apparatus for sterilizing objects according to the present invention;

FIG. 2 is a cross-sectional view of the apparatus of FIG. 1, taken along line 2—2 thereof;

DETAILED DESCRIPTION OF THE PREFERRED EMBODIMENTS

Figure 3:
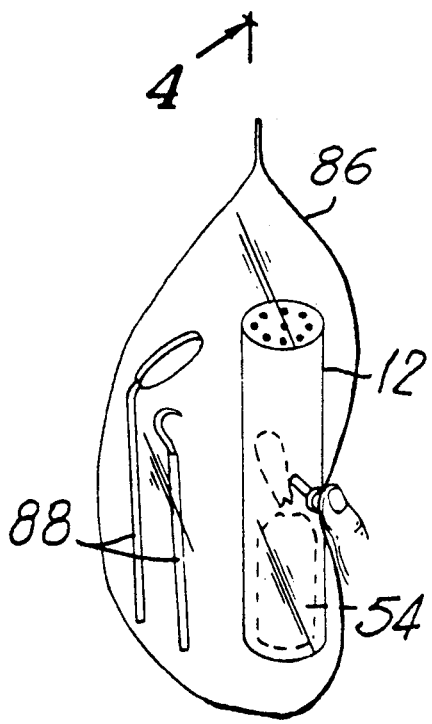
FIG. 3 is a perspective view showing a first use of the apparatus of FIG. 1, for sterilizing dental instruments.

Referring to the drawings in detail, and initially to FIGS. 1 and 2 thereof, apparatus 10 for sterilizing objects, such as surgical, medical, dental and other instruments, according to one embodiment of the present invention, includes a cartridge 12, preferably molded from a rigid plastic material, such as high impact polystyrene. Cartridge 12 includes an elongated cylindrical test-tube like outer shell 14 formed by an elongated tubular wall 16 having a lower section 18 with a first wall thickness and an upper coaxial and contiguous section 20 with a second wall thickness which is less than the first wall thickness of lower section 18. The outer diameters of lower section 18 and upper section 20 may be identical so that outer shell 14 has a smooth and continuous outer wall. Accordingly, an inner annular shoulder 22 is formed between lower section 18 and upper section 20, as shown best in FIG. 2.

Outer shell 14 further includes a bottom wall 24 which closes off the lower end of lower section 18, while the upper end 26 of upper section 20 is open. In addition, a radially extending bore 28 is formed in lower section 18, just below annular shoulder 22.

Cartridge 12 further includes an elongated cylindrical test-tube like inner shell 30 formed by an elongated tubular wall 32 having a bottom wall 34 which closes off the lower end of tubular wall 32 and an open upper end 36. The outer diameter of tubular wall 32 of inner shell 30 is similar to the inner diameter of tubular wall 16 of outer shell 14, in order to permit inner shell 30 to slide freely within upper section 20 of outer shell 14. Accordingly, as shown best in FIG. 2, inner shell 30 is slid within upper section 20 of outer shell 14, until bottom wall 34 of inner shell 30 rests on annular shoulder 22.

Further, the length of tubular wall 32 of inner shell 30 is slightly less than the length of tubular wall 16 of outer shell 14. Accordingly, when inner shell 30 is fully slid into upper section 20 of outer shell 14, open upper end 36 of inner shell 30 is positioned slightly lower than open upper end 26 of upper section 20 of outer shell 14. Accordingly, an annular shoulder 38 is formed by open upper ends 26 and 36. In addition, an axially extending hole 40 is formed centrally in bottom wall 34.

Cartridge 12 further includes a perforated closure cap 42 having a main disk body 44 and an outer annular flange 46 connected with and in surrounding relation to main disk body 44. Main disk body 44 is provided with a plurality of holes 47 therein. As shown in FIGS. 1 and 2, eight holes 47 are provided in a circular arrangement in main disk body 44 about a center hole 47.

Main disk body 44 has an outer diameter substantially equal to the inner diameter of outer shell 14 so as to fit therein and seat on annular shoulder 38, while annular flange 46 has an outer diameter substantially equal to the outer diameter of outer shell 14 so as to seat on the open upper end 26 thereof. In addition, main disk body 44 has a predetermined thickness, while upper annular flange 46 has a thickness less than the thickness of main disk body 44. However, because the upper surfaces of main disk body 44 and outer annular flange 46 are coplanar, a lower annular shoulder 48 is formed between main disk body 44 and outer annular flange 46 at the periphery of the undersurface of closure cap 42. As a result, when flange 46 seats on open upper end 26 of outer shell 14, the lower portion of main disk body 44 fits within open upper end 26 of outer shell 14 and seats on annular shoulder 38, while annular flange 46 seats on open upper end 26. Preferably, closure cap 42 is secured to open upper end 26 of outer shell 14 by melting and bonding using ultrasonic energy.

With this arrangement, as shown best in FIG. 2, a lower compartment or chamber 50 is defined by lower section 18, bottom wall 24 and bottom wall 34, while an upper compartment or chamber 52 is defined by tubular wall 32 and bottom wall 34 of inner shell 30, along with closure cap 42.

An ampule 54 is adapted to be held within lower chamber 50. In this regard, ampule 54 is a sealed gas-tight container made from a breakable material, such as glass, which contains a sterilant therein, and which is impervious to the sterilant. Ampule 54 is formed by a main body 56 and a spout 58 connected to main body 56 by a reduced diameter neck 60, which is scored along a score line 62, to facilitate breaking open of ampule 54. The sterilant is preferably ethylene oxide, although any other suitable sterilant can be used. The ethylene oxide is maintained largely in a liquid state when sealed in ampule 54.

In order to prevent accidental breaking of ampule 54 during shipping, a lower sponge disk 64 is provided in the bottom of lower chamber 50 for supporting ampule 54 thereon, and an upper sponge disk 66 is provided at the upper end of lower chamber 50 above ampule 54. Sponge disks 64 and 66 are sufficiently porous to permit liquid and gas flow therethrough, while also providing cushioning of ampule 54 in lower chamber 50.

At the same time, upper chamber 52 is packed with absorbent cotton wool 68 or similar material which absorbs the liquid ethylene oxide and permits it to slowly vaporize. Accordingly, when ampule 54 is broken, the gaseous ethylene oxide is released in lower chamber 50 and passes through upper sponge disk 66, axially extending hole 40 in inner shell 30, cotton wool 68 and holes 47 in closure cap 42. The liquid ethylene oxide is forced by the vapor pressure of the ethylene oxide in lower chamber 50 through upper sponge disk 66 and axially extending hole 40, where it is then held by absorbent cotton wool 68 in upper chamber 52, and thereby does not spray out of holes 47 in closure cap 42. The liquid ethylene oxide held by absorbent cotton wool 68 absorbs heat from the surroundings and is thereby converted into a gas at a rapid rate.

In accordance with one aspect of the present invention, ampule 54 is broken by means of a push-button 70 slidably fit within radially extending bore 28. Push-button 70 includes a stem 72 slidably fit within radially extending bore 28 and an enlarged disk-shaped head 74 formed at the end of stem 72 extending out of cartridge 12. Push-button 70 can be made, for example, from a high impact polystyrene material or the like. In this manner, the extent to which push-button 70 can be inserted within cartridge 12 is restricted by enlarged head 74.

Thus, when push-button 70 is pushed inwardly of cartridge 12, the opposite free end of stem 72 applies a force against spout 58. Because main body 56 of ampule 54 has a similar diameter to the inner diameter of lower section 18, main body 56 is held therein. Accordingly, the force applied by stem 72 results in the breaking of reduced diameter neck 60 along score line 62, whereby the gaseous and liquid ethylene oxide escape to cotton wool 68, as aforementioned.

Figure 5:
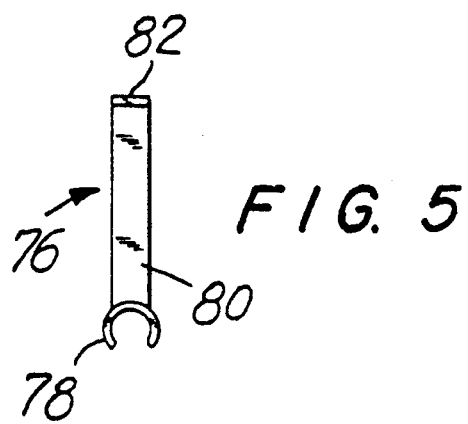
FIG. 5 is a front elevational view of the trigger guard of the apparatus of FIG. 1.

In order to prevent accidental depression of push-button 70, apparatus 10 further includes a trigger guard 76. Specifically, as shown best in FIGS. 1, 2 and 5, trigger guard 76 includes a substantially C-shaped snap-lock 78 having an inner diameter substantially equal to the outer diameter of stem 72. Accordingly, snap-lock 78 can be snap fit over stem 72 and held thereon. Snap-lock 78 has a width sufficient to maintain the free end of stem 72 in spaced relation to spout 58 when snap-lock 78 is positioned over stem 72, as shown best in FIG. 2.

In order to remove trigger guard 70 from stem 72, trigger guard 70 further includes a removal bar 80 connected with snap-lock 78 at one edge thereof, such that removal bar 80 can be positioned substantially flat against the outer surface of outer shell 14 when snap-lock 78 is fit over stem 72. A piece of adhering tape 81 or the like is provided to retain removal bar 80 in a releasably fixed position on cartridge 12, as shown in FIGS. 1 and 2.

A finger grip 82 is connected at the opposite end of removal bar 80 and extends outwardly of outer shell 14. Accordingly, when tape 81 is removed, a user can remove snap-lock 78 from stem 72 by pulling finger grip 82 in the vertically upward direction of FIG. 2, away from stem 72. Accordingly, the open ends of snap-lock 78 will deform outwardly and ride over stem 72. Once snap-lock 78 is removed, stem 72 can be pushed inwardly of cartridge 12 to break ampule 54.

Figure 4:
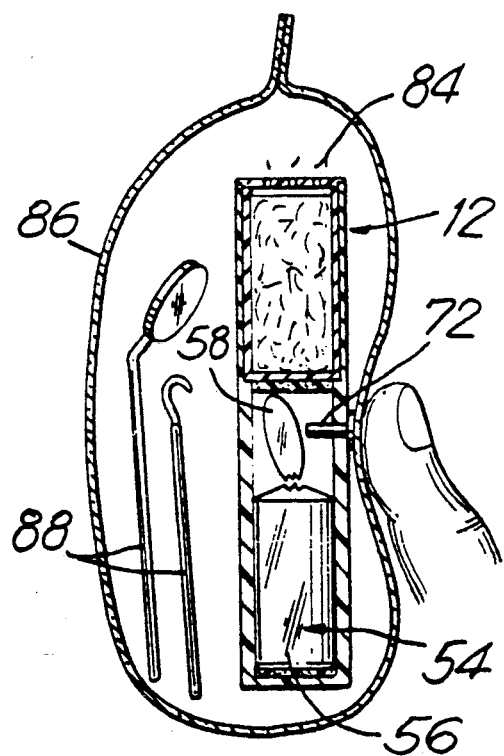
FIG. 4 is a cross-sectional view of the apparatus of FIG. 3, taken along line 4—4 thereof.

In operation, and referring to FIGS. 3 and 4, tape 81 is removed, whereupon the user grasps finger grip 82 and pulls up on trigger guard 76, so as to remove snap-lock 78 from stem 72. Then, cartridge 12 is inserted and hermetically heat sealed within a liner bag 86, along with instruments 88 to be sterilized. The user then grasps cartridge 12 through bag 86, and merely depresses push-button 70 so that the free end of stem 72 snaps ampule 54 along score line 62.

Ethylene oxide gas and liquid are then released into lower chamber 50, and because of the vapor pressure of the ethylene oxide, are forced through hole 40 in bottom wall 34 of inner shell 30. The liquid is retained by absorbent cotton wool 68 in upper chamber 52, while the gas passes relatively unhindered through holes 47 in closure cap 42, into liner bag 86 to sterilize instruments 88. The liquid ethylene oxide held by cotton wool 68 absorbs heat from its surroundings and is converted to a gas at a rapid rate. This gas then also escapes through holes 47 to further sterilize instruments 88.

Figure 6:
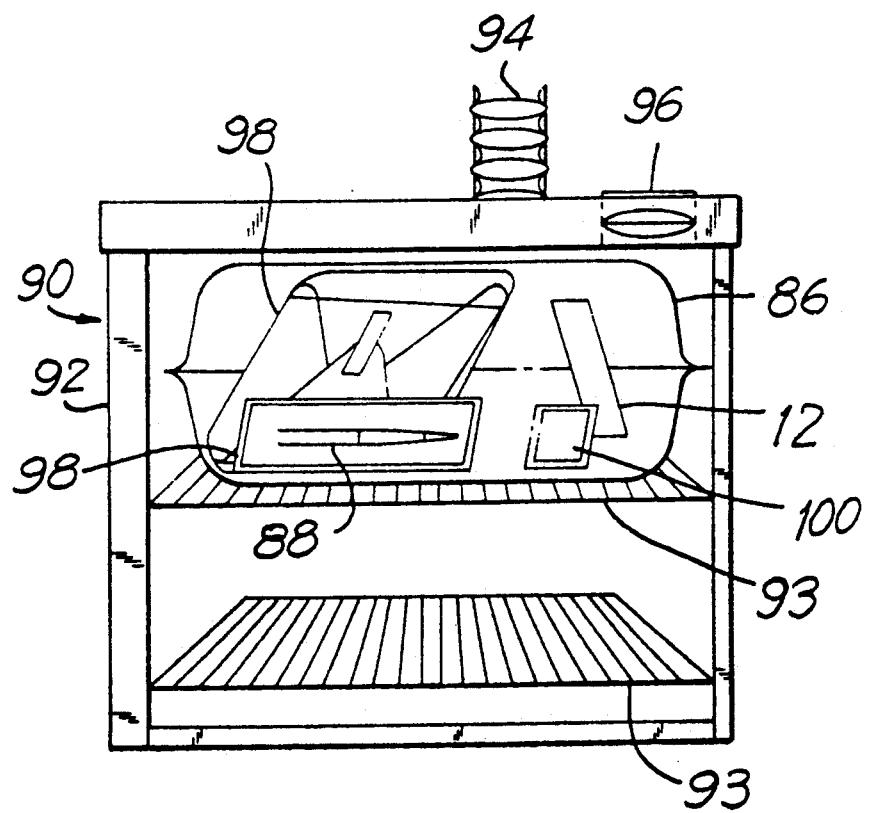
FIG. 6 is a schematic perspective view showing another use of the apparatus of FIG. 1, for sterilizing medical instruments.

Referring now to FIG. 6, an alternative operation showing a modified use of apparatus 10 will now be described. Specifically, apparatus 10 is used with a system 90 similar to that disclosed in the aforementioned commonly assigned U.S. Pat. No. 4,937,046.

System 90 includes a container 92 having shelf racks 93 therein. Container 92 further includes a gas outlet port 94 by which the gaseous ethylene oxide that passes through liner bag 86 can be removed to ambient atmosphere, and an air intake port 96 by which air can be supplied to the interior of container 92 during a purge cycle. With system 90, because of the use of container 92, a larger liner bag 86 can be used. Further, instruments 88 are preferably wrapped by a porous wrapping material 98 before being placed within liner bag 86. Still further, a humidifying device 100 is placed inside liner bag 86 for raising the relative humidity to a required level, for example, as taught in the aforementioned copending U.S. Pat. No. 5,082,636.

The operation is virtually identical with system 90. Thus, after cartridge 12 is inserted within liner bag 86, the ampule is broken in the manner discussed above. Liner bag 86 is then placed within container 92, and the gas that escapes from liner bag 86 is exhausted from container 92 through gas outlet port 94.

Therefore, it will be appreciated that the present invention permits easy and ready breaking of ampule 54 while the ampule is in liner bag 86.

In addition, the gas is instantly released into the liner bag and the sterilization cycle begins immediately, unlike the aforementioned known arrangements which require the use of a gas release bag within the liner bag. Thus, the present invention eliminates the need for a gas release bag. It will be appreciated that the liner bag serves two functions, namely to contain the items to be sterilized along with the ethylene oxide gas and to protect the operator from exposure to ethylene oxide from the time push-button 70 is pushed and the time the liner bag is placed within protective container 92, which is typically one to two minutes. The liner bag is a gas diffusion membrane which retains the ethylene oxide gas long enough to sterilize its contents and then allows the gas to diffuse into container 92 from which it is vented harmlessly to the outside atmosphere.

In the aforementioned known arrangement where a gas release bag is used, no ethylene oxide is released by the gas release bag for about 15 minutes after the ampule has been broken and the peak concentration of ethylene oxide is reached in about 3 hours. According to the present invention, a gas release bag is not used, and the peak concentration of ethylene oxide is reached in about 15 minutes.

It will be noted that the present invention is intended to operate at elevated temperatures of about 50° C., and in the total operation takes about 16 hours, as compared with about 38 hours in the aforementioned known devices. In order to obtain such shortened time of operation, it is necessary to inject the ethylene oxide gas more quickly. This is accomplished by using cartridge 12 and by eliminating the gas release bag.

Further, in such a system, because of the faster operation, a lower concentration of ethylene oxide gas can be used. This reduces the absorption of the ethylene oxide gas by the products in the liner bag, whereby the products will air out faster. The elevated temperature produces a quicker killing of the microorganisms and also results in quicker aeration of the absorbent materials. It is noted, however, that because the sterilization and aeration temperatures are elevated, water vapor is added to the system to prevent the production of desiccated organisms that are very difficult to sterilize with ethylene oxide. In this regard, humidifying device 100 preferably maintains the contents of the liner bag at a relative humidity greater than 30% at 50° C.

Further, with the present invention, push-button 70, cartridge 12 and ampule 54 can be shipped as a unit. This is because push-button 70 is locked during shipping, to prevent accidental breaking of ampule 54. Still further, push-button 70 does not substantially increase the size and cost of apparatus 10.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

What is claimed is:

1. Apparatus for releasing a gaseous sterilant to sterilize objects comprising:

a sealed ampule containing a liquid sterilant;

cartridge means for holding the sealed ampule in a substantially immovable manner, said cartridge means including a transverse bore and at least one outlet opening;

push-button means slidably movable in said transverse bore for breaking open the ampule upon depression of said push-button means in said transverse bore;

wherein, upon breaking open the ampule, said gaseous sterilant escapes from the ampule through said at least one outlet opening into sterilizing contact with the objects;

said cartridge means including first chamber means for containing the ampule therein, and second chamber means for holding an absorbent material therein to hold said liquid sterilant upon breaking open of the ampule;

said cartridge means further including:

an outer tubular shell having a closed first end and an open second end;

an inner tubular shell having a transverse third end and an open fourth end, said inner tubular shell being inserted partially within said outer tubular shell through said open second end of said outer tubular shell such that said first chamber means is defined by said outer tubular shell, said closed first end, and said transverse third end, said second chamber means being partially defined by said inner tubular shell and said transverse third end, said transverse third end including at least one opening providing communication between said first and second chamber means; and cap means on said open second and fourth ends, said second chamber means being partially defined by said cap means, said cap means including said at least one outlet opening therein.

2. Apparatus according to claim 1, wherein said outer tubular shell includes shoulder means for defining the extent that said inner tubular shell is inserted into said outer tubular shell.

3. Apparatus according to claim 1, wherein said transverse bore is formed through said outer tubular shell at a position beneath said shoulder means.

4. Apparatus according to claim 1, further including cushioning means for cushioning the ampule in said first chamber means.

5. Apparatus according to claim 4, wherein said cushioning means includes sponge disk means positioned on opposite ends of the ampule in said first chamber means.

6. Apparatus according to claim 1, wherein said push-button means includes stem means slidably movable in said transverse bore for breaking open the ampule upon depression of said push-button means in said transverse bore, and head means connected with said stem means for limiting slidable movement of said stem means in said transverse bore.

7. Apparatus according to claim 6, further including guard means for preventing breaking of the ampule by said stem means.

8. Apparatus for releasing a gaseous sterilant to sterilize objects comprising:

a sealed ampule containing a liquid sterilant;

cartridge means for holding the sealed ampule in a substantially immovable manner, said cartridge means including a transverse bore and at least one outlet opening;

push-button means including stem means slidably movable in said transverse bore for breaking open the ampule upon depression of said push-button means in said transverse bore, and head means connected with said stem means for limiting slidable movement of said stem means in said transverse bore;

wherein, upon breaking open the ampule, said gaseous sterilant escapes from the ampule through said at least one outlet opening into sterilizing contact with the objects; and guard means including snap-lock means in releasable engagement with said stem means for preventing slidably movement of said stem means in said transverse bore a sufficient distance to break the ampule.

9. Apparatus according to claim 8, wherein said guard means includes disengagement means for disengaging said snap-lock means from said stem means to permit slidable movement of said stem means in said transverse bore a sufficient distance to break the ampule.

10. Apparatus according to claim 9, wherein the ampule includes a main body, a spout and a reduced diameter neck which connects the main body and the spout, with said reduced diameter neck having a weakened section which constitutes said breakable section, and said stem means is positioned to engage said spout when said stem means is depressed in said transverse bore, so as to break the ampule along the weakened section.

11. Apparatus according to claim 9, further including restraining means for releasably holding said guard means on said cartridge means.

12. Apparatus for releasing a gaseous sterilant to sterilize objects comprising:

a sealed ampule containing a liquid sterilant;

cartridge means for holding the sealed ampule in a substantially immovable manner, said cartridge means including a transverse bore and at least one outlet opening;

push-button means slidably movable in said transverse bore for breaking open the ampule upon depression of said push-button means in said transverse bore;

wherein, upon breaking open the ampule, said gaseous sterilant escapes from the ampule through said at least one outlet opening into sterilizing contact with the objects; and flexible bag means for holding said cartridge means and the objects to be sterilized in a sealed manner, wherein said push-button means can be depressed through said flexible bag means;

said cartridge means including first chamber means for containing the ampule therein, and second chamber means for holding an absorbent material therein to hold said liquid sterilant upon breaking open of the ampule;

said cartridge means further including:

an outer tubular shell having a closed first end and an open second end;

an inner tubular shell having a transverse end and an open fourth end, said inner tubular shell being inserted partially within said outer tubular shell through said open second end of said outer tubular shell such that said first chamber means is defined by said outer tubular shell, said closed first end, and said transverse third end, said second chamber means being partially defined by said inner tubular shell and said transverse third end, said transverse third end including at least one opening providing communication between said first and second chamber means; and closure cap means for closing said open second and fourth ends of said outer and inner tubular shells, respectively, said closure cap means including said at least one outlet opening therein.

13. Apparatus for releasing a gaseous sterilant to sterilize objects comprising:

a sealed ampule containing a liquid sterilant;

cartridge means for holding the sealed ampule in a substantially immovable manner, said cartridge means including a transverse bore and at least one outlet opening;

push-button means including stem means slidably movable in said transverse bore for breaking open the ampule upon depression of said push-button means in said transverse bore, and head means connected with said stem means for limiting slidably movement of said stem means in said transverse bore;

wherein, upon breaking open the ampule, said gaseous sterilant escapes from the ampule through said at least one outlet opening into sterilizing contact with the objects;

flexible bag means for holding said cartridge means and the objects to be sterilized in a sealed manner, wherein said push-button means can be depressed through said flexible bag means; and guard means including snap-lock means in releasable engagement with said stem means for preventing slidable movement of said stem means in said transverse bore a sufficient distance to break the ampule.

14. Apparatus according to claim 13, wherein said guard means includes disengagement means for disengaging said snap-lock means from said stem means to permit slidable movement of said stem means in said transverse bore a sufficient distance to break the ampule.

15. Apparatus according to claim 13, wherein the ampule includes a main body, a spout and a reduced diameter neck which connects the main body and the spout, with said reduced diameter neck having a weakened section, and said stem means is positioned to engage said spout when said stem means is depressed in said transverse bore, so as to break the ampule along the weakened section.

16. Apparatus for releasing a gaseous sterilant to sterilize objects comprising:

a sealed ampule containing a liquid sterilant;

cartridge means for holding the sealed ampule in a substantially immovable manner, said cartridge means including a transverse bore and at least one outlet opening;

push-button means including stem means slidably movable in said bore for breaking open the ampule upon depression of said push-button means in said bore, and head means connected with said stem means for limiting slidable movement of said stem means in said bore, such that upon breaking open the ampule, said sterilant escapes from the ampule through said at least one outlet opening into sterilizing contact with the objects;

guard means for preventing breaking of the ampule by said stem means, said guard means including means in releasable engagement with said push-button means for preventing slidable movement of said stem means in said transverse bore a sufficient distance to break the ampule.

17. Apparatus for releasing a sterilant to sterilize objects comprising:

a sealed ampule containing a sterilant in liquid form;

cartridge means having a first chamber and a second chamber, said ampule being disposed in said first chamber;

absorbing means in said second chamber;

communication means in said cartridge means providing communication between said first and second chambers;

breaking means on said cartridge means and movably manipulatable externally of said cartridge means to effect breaking of said ampule in said first chamber such that upon breaking of said ampule, the liquid sterilant is released from the broken ampule and passes through said communication means to said absorbing means, said absorbing means being operably to absorb said liquid sterilant and thereby facilitate conversion of the liquid sterilant into a gaseous state; and passageway means on said cartridge means for the gaseous sterilant in gaseous state to pass from said second chamber to sterilize said objects.

18. Apparatus according to claim 17 wherein said absorbing means comprises cotton.

* * * * *